United States Patent [19]

Gastmeier et al.

[11] Patent Number: 4,553,627

[45] Date of Patent: Nov. 19, 1985

[54] HEARING AID WAX GUARD

[75] Inventors: William J. Gastmeier, Waterloo; Rolf Dohmer, Kitchener, both of Canada

[73] Assignee: Unitron Industries, Kitchener, Canada

[21] Appl. No.: 663,735

[22] Filed: Oct. 22, 1984

[51] Int. Cl.[4] .......................... A61B 7/02; H04R 25/02

[52] U.S. Cl. .................................... 181/135; 181/130; 179/107 E; 128/152

[58] Field of Search ........................ 181/130, 133, 135; 179/107 E, 182 R, 182 A; 128/152

[56] References Cited

U.S. PATENT DOCUMENTS 1,830,198 11/1931 French ........................ 179/182 R X 3,934,100 1/1976 Harada ............................ 179/182 R 4,349,082 9/1982 Gastmeier ........................... 181/130

*Primary Examiner*—Benjamin R. Fuller

*Attorney, Agent, or Firm*—Rogers, Bereskin & Parr

[57] ABSTRACT

A wax guard for a hearing aid is mushroom-shaped, having a cross passage through its head which intersects an axial passage in its stem. The axial passage contains an acoustic filter terminating the axial passage in its characteristic impedance. The cross passage is semi-circular in section to reduce the projection of the guard into an ear canal and the total area of the two branches of the passage exiting from the axial passage is equal to that of the axial passage. The guard removably snap fits into a metal ring glued into the outlet port of the hearing aid.

8 Claims, 5 Drawing Figures

HEARING AID WAX GUARD

FIELD OF THE INVENTION

This invention relates to an improved wax guard for a hearing aid.

BACKGROUND OF THE INVENTION

Hearing aids conventionally have a tubing portion which enters the user's ear to deliver sound into the ear. The opening at the end of the tubing can become plugged with ear wax, and therefore it is known to fit a wax guard at the end of the tubing. The wax guard is a small piece having an axial hole and can be removed for cleaning.

Existing wax guards have several disadvantages. In many cases they do not adequately prevent wax from entering the hearing aid tubing, and if this occurs, the hearing aid must be disassembled to clean the tubing. If the tubing is fitted with an acoustic filter, and if the filter becomes clogged, then the entire piece of tubing must be discarded or else the filter must be removed therefrom and replaced, both relatively costly operations. In addition, previous wax guards frequently fell out into the ear canal during hearing aid insertion or removal.

BRIEF SUMMARY OF INVENTION

Accordingly, it is an object of the present invention to provide a wax guard which provides improved protection against wax entering the hearing aid tubing, and which also includes an acoustic filter in the wax guard itself. In one aspect the invention provides a wax guard comprising:

(a) a head of substantially circular configuration as viewed from one end thereof, (b) a stem projecting axially from the other end of said head and being integral with said head, said stem having a substantially circular cross section and being of smaller diameter than that of said head, (c) said head having a cross passage extending therethrough, said cross passage having in cross section a substantially planar lower surface adjacent said other end of said head and having a domed upper surface, (d) said stem having an axial passage extending therethrough and intersecting said cross passage in said head, (e) an acoustic filter located in said axial passage and clear of said cross passage to allow a cleaning instrument to be pushed through said cross passage, and (f) said stem having a free end having a flared resilient tip adapted to secure said stem within an opening of a hearing aid.

In another aspect the invention provides in a hearing aid having a plastic shell, a transducer within said shell, an outlet port adapted to be located within an ear, and tubing connecting said transducer with said outlet port, the improvement comprising a metal ring adhered within said outlet port, and a wax guard removably fitted within said ring, said wax guard comprising:

(a) a head having a cross passage extending therethrough, (b) a stem projecting from said head, said stem being integral with said head and of small diameter than said head, (c) said stem having an axial passage therethrough intersecting said cross passage in said head, (d) said stem having a flared tip adapted to secure said stem within an opening of a hearing aid, and (e) an acoustic filter located in said axial passage and clear of said cross passage to allow a cleaning instrument to be pushed through said cross passage.

BRIEF DESCRIPTION OF THE DRAWINGS

Futher objects and advantages of the invention will appear from the following description, taken together with the accompanying drawings in which.

DETAILED DESCRIPTION OF PREFERRED EMBODIMENTS OF THE INVENTION

Figure 1:
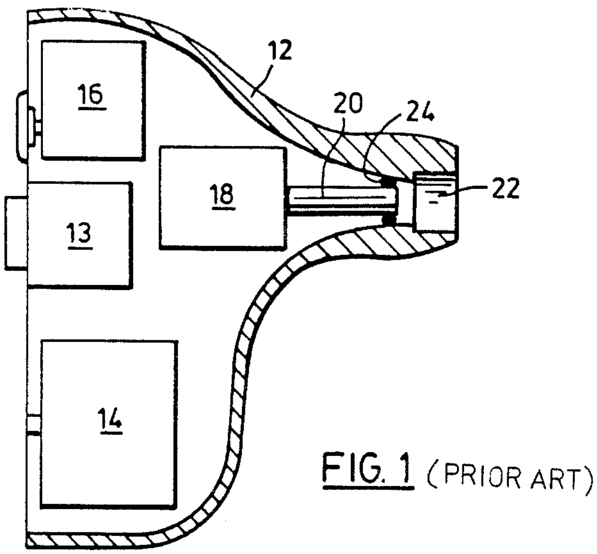
FIG. 1 (PRIOR ART)
FIG. 1 is a cross-sectional view of a prior art conventional hearing aid.

FIG. 1 shows a conventional "in the ear" hearing aid 10 which fits entirely within the user's ear. The hearing aid 10 includes a plastic shell 12 having therein a battery compartment 13, a microphone 14 which receives sound to be amplified, an amplifier 16 connected to the microphone 14 by wiring not shown to amplify sound picked up by the microphone, and a receiver 18 (in fact a miniature loudspeaker in a box) to receive the amplified signal from the amplifier 16 and to transduce such signal into sound. The sound produced by the receiver 18 is transmitted through a flexible tube 20 and through an outlet port 22 in the shell 12, into the user's ear. The flexible tubing 20 is glued at 24 to the plastic shell 12 and may also be glued to the receiver 18.

In the arrangement shown, wax can enter the outlet port 22 in the shell 12 and can clog the receiver tube. In addition, because the shell is molded to fit individual ears, the length of tubing 20 can vary causing an unpredictable frequency response.

The invention therefore provides a wax guard, a preferred embodiment of which is shown in the drawings and indicated at 26, to fit into the outlet port 22. The wax guard 26 is generally mushroom-shaped, having a stem 28 and a head 30 integral with stem 28. The head 30 is of circular configuration as viewed axially and has a domed top 32 as viewed from the side. The head 30 further includes a cylindrical side wall 34 which extends parallel to the axis of the head 30.

A cross passage 36 extends entirely through the head 30 and intersects an axial passage 38 in the stem 28. The passage 38 in the stem extends through the free end 40 of the stem.

Figure 4:
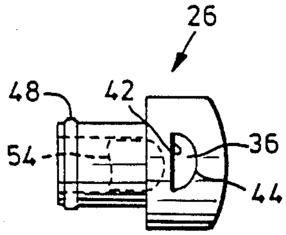
FIG. 4 is a side view of the wax guard of FIG. 3.
Figure 5:
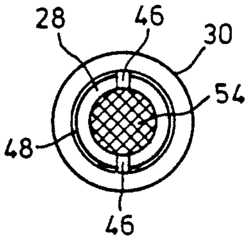
FIG. 5 is an end view of the wax guard of FIG. 3.

As best shown in FIG. 4, the cross passage 36 is semicircular in cross-section, having a planar lower surface 42 adjacent the stem 28 and having a domed upper surface 44. This cross section allows the height of the head 30 to be reduced, so that the wax guard 26 will project as short a distance as possible into the user's ear canal. However the diameter of the cross passage 36 (i.e. the width of its lower surface 42) is substantially the same as the diameter of the axial passage 38. Therefore the total area of the two outlets constituted by the two openings of cross passage 36 at the sidewall 34 is substantially the same as the cross-sectional area of the axial passage 38 (since the cross passage 36 is semi-circular in section). This improves the impedance match between the two passages, thus reducing sound transmission losses and distortion.

Figure 2:
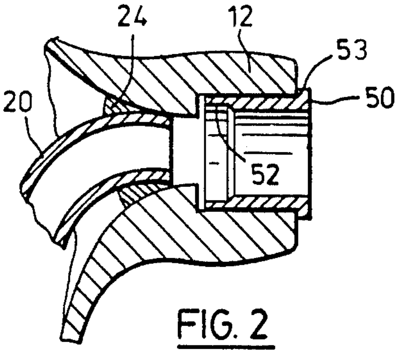
FIG. 2 is a cross-sectional view of the tip of the hearing aid of FIG. 1, showing a metal ring according to the invention glued therein.
Figure 3:
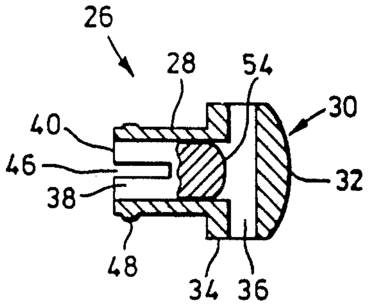
FIG. 3 is a cross-sectional view of a wax guard according to the invention.

The wall of the stem 28 includes two slots 46 formed therein at the free end 40. An external rounded ridge 48 is also formed adjacent the top of end 40. The slots 46 allow the free end of the stem 28 to be compressed slightly to slide snugly into a metal ring 50 (FIG. 2) which is glued into the outlet port 22. When the stem 28 has been fully slid into ring 50, the compressed free end 40 expands and ridge 48 snaps into a circumferential recess 52 of increased internal diameter formed at the inner end of ring 50. This removably locks the wax guard 26 into the metal ring 50. The metal ring 50 includes a small lip 53 to position it within the outlet port 22.

Located within the axial passage 38 of the wax guard 26 is an acoustic filter 54 of the kind shown in U.S. Pat. No. 4,349,082 issued Sept. 14, 1982 and entitled "ACOUSTICAL DAMPING ELEMENT AND METHOD OF FORMING SAME" and assigned to the assignee of the present invention. That patent describes an acoustic filter consisting of a layer of fabric and a layer of metal screen which are pressed into a tubing by a punch to form a cup-shaped filter in which the screen holds the fabric pressed against the side walls of the tubing. In the present case, the layer of fabric is formed by a metal screen so that the filter consists of two layers of metal screen both of the same size mesh and effectively forming two impedances in series. The filter 54 is preferably located in the stem 28 axially displaced from the slots 46, so that compression of the stem 28 at the slots 46 will not loosen the fit of the filter. The filter is also clear of the cross passage 36, so that a cleaning instrument inserted through the cross passage 36 will not catch the filter 54.

The wax guard arrangement shown has a number of advantages. Firstly, the use of a cross passage intersecting an axial passage reduces the likelihood that ear wax can enter the axial passage 38 and clog the filter 54. In fact, it is found that ear wax is generally of a consistency such that when a cleaning tool is inserted through the cross passage 36, the cleaning tool simply pushes the ear wax out of the passage without the wax being caught in the filter 54.

Secondly, the wax guard 26 can easily be removed from the hearing aid for cleaning or replacement (by a reasonably hard pull), and yet when it is inserted into the hearing aid, it is held in position by the rounded ridge 48 and recess 52 so that it cannot readily fall out into the user's ear canal. It will be appreciated that the parts shown are greatly expanded in size in the drawings and in fact are extremely tiny, as shown in Table I at the end of this description, so that if the wax guard were to fall into an ear canal, it could be extremely difficult to remove.

Further, in a hearing aid of the kind shown which is individually molded and fitted to the user's ear, the tubing 20 can vary substantially in length, in some cases by 30 or 40 percent. The variation in the length of tube 20 can cause an unpredictable frequency response. The filter 54 terminates the tubing 20 in its characteristic impedance (which depends primarily on the diameter of the tubing), removing its resonances and helping to provide a predictable frequency response independent of tubing length.

The acoustic filter 54, also located in the wax guard, has the added advantage that if an unusually large quantity of wax or other secretions find their way into the axial passage 38, the filter 54 will block such matter before it enters the tube 20. The entire wax guard 26, which is small and inexpensive, can then be thrown away and replaced by a fresh wax guard with its filter 54. Alternatively, the filter 54 can be removed, the wax guard cleaned and a fresh filter 54 inserted, but normally the user and the hearing aid service centre will lack the facilities for inserting a fresh filter and the cost of replacing the tiny wax guard would usually be very small.

A further advantage of the arrangmeent shown is that the metal ring 50 provides a consistent output port diameter which can be used to attach the hearing aid to a test fixture (not shown) to test the performance of the hearing aid. Without the metal ring 50, the diameter of the outlet port 22 is not normally well enough controlled to allow reliable testing with no acoustic leaks and in any event may wear after several insertions of test instruments, thereby causing acoustic leaks.

The wax guard 26 can be formed in various ways but is preferably injection molded from a suitable plastic. Typical dimensions of a preferred embodiment of the invention are given in Table I which follows.

TABLE I

| Part and Number | Size (Inches) |
|---|---|
| Diameter of head 30 | .115 |
| Height of head 30 | .070 |
| Length of stem 28 | .080 |
| External diameter of stem 28 | .075 |
| Width (maximum diameter) of cross passage 36 | .025 |
| Diameter of axial passage 38 | .050 |
| Length of slot 46 | .050 |
| External diameter of ring 50 | .100 |
| Length of ring 50 | .080 |

We claim:

1. A wax guard comprising:
(a) a head of substantially circular configuration as viewed from one end thereof,
(b) a stem projecting axially from the other end of said head and being integral with said head, said stem having a substantially circular cross section and being of smaller diameter than that of said head,
(c) said head having a cross passage extending therethrough, said cross passage having in cross section a substantially planar lower surface adjacent said other end of said head and having a domed upper surface,
(d) said stem having an axial passage extending therethrough and intersecting said cross passage in said head,
(e) an acoustic filter located in said axial passage and clear of said cross passage to allow a cleaning instrument to be pushed through said cross passage, and
(f) said stem having a free end having a flared resilient tip adapted to secure said stem within an opening of a hearing aid.

2. A wax guard according to claim 1 and including a metal ring adapted to be fastened within said opening of said hearing aid, said ring being of a diameter to receive said stem and having an enlarged end adapted to receive said flared end of said stem to retain said stem removably within said ring.

3. A wax guard according to claim 2 wherein said stem includes at least two slots in said free end, to facilitate compression of said flared tip for insertion of said stem within said ring.

4. A wax guard according to claim 3 wherein said acoustic filter is located clear of said slots, between said slots and said cross passage.

5. A wax guard according to claim 4 wherein said acoustic filter has the shape of a cup-shaped element.

6. A wax guard according to claim 1 wherein the cross-sectional area of said cross passage is substantially one half that of said axial passage.

7. In a hearing aid having a plastic shell, a transducer within said shell, an outlet port adapted to be located within an ear, and tubing connecting said transducer with said outlet port, the improvement comprising a metal ring adhered within said outlet port, and a wax guard removably fitted within said ring, said wax guard comprising:

(a) a head having a cross passage extending therethrough, (b) a stem projecting from said head, said stem being integral with said head and of small diameter than said head, (c) said stem having an axial passage therethrough intersecting said cross passage in said head, (d) said stem having a flared tip adapted to secure said stem within an opening of a hearing aid, and (e) an acoustic filter located in said axial passage and clear of said cross passage to allow a cleaning instrument to be pushed through said cross passage.

8. Apparatus according to claim 7 wherein said stem includes at least two slots therein so that said stem may be compressed for insertion into said ring, said ring having an enlarged end adapted to receive said flared end of said stem to retain said stem removably within said ring.

* * * * *